United States Patent

Waki et al.

Patent Number: 5,977,257
Date of Patent: Nov. 2, 1999

[54] POLYMER MATERIAL, MEDICAL MATERIAL AND LIQUID HIGH MOLECULAR COMPOSITION

[75] Inventors: Kazunori Waki; Daijiro Shiino; Kazuo Matsuyama, all of Tsukuba; Nobuo Nakabayashi, Matsudo; Kazuhiko Ishihara, Kodaira, all of Japan

[73] Assignees: NOF Corporation, Tokyo; Japan Science and Technology Corporation, Kawaguchi; Nakabayashi, Nobou, Matsudo; Ishihara, Kazuhiko, Kodaira, all of Japan

[21] Appl. No.: 08/945,741
[22] PCT Filed: Mar. 25, 1996
[86] PCT No.: PCT/JP96/00769
  § 371 Date: Oct. 28, 1997
  § 102(e) Date: Oct. 28, 1997
[87] PCT Pub. No.: WO96/34061
  PCT Pub. Date: Oct. 31, 1996

[30] Foreign Application Priority Data

Apr. 28, 1995 [JP] Japan ................................. 7-105920

[51] Int. Cl.$^6$ ......................... C08L 75/04; C08J 3/28
[52] U.S. Cl. ........................... 525/131; 522/79; 522/111; 526/276; 526/277; 525/100; 525/148; 525/154; 525/175; 525/183; 525/189; 525/197; 525/209
[58] Field of Search .......................... 525/131; 526/277, 526/276; 522/111, 79

[56] References Cited

FOREIGN PATENT DOCUMENTS

WO 94/14897  7/1994  WIPO.

Primary Examiner—Patricia A. Short
Attorney, Agent, or Firm—Darby & Darby

[57] ABSTRACT

A high molecular material and a medical material which is a mixed material containing a copolymer A produced by copolymerization of a monomer composition containing a monomer having a side chain represented by the formula (1)

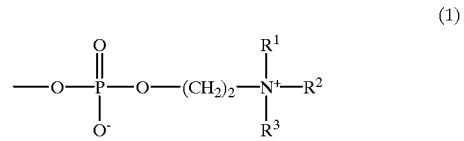

($R^1$, $R^2$, $R^3$; H or a C1–4 alkyl group) and a hydrophobic monomer, and one or more sorts of hydrophobic polymer B other than the copolymer A; wherein structure of said mixed material shows phase separation in which domains of several hundred micrometers or less in size consisting of the copolymer A are uniformly distributed in a phase consisting of said hydrophobic polymer B. A liquid high molecular composition in which the copolymer A and the hydrophobic polymer B are dissolved in a mixed solvent consisting of a halogenated hydrocarbon solvent and a lower alcohol solvent, which has turbidity of 60% or less.

6 Claims, 1 Drawing Sheet

POLYMER MATERIAL, MEDICAL MATERIAL AND LIQUID HIGH MOLECULAR COMPOSITION

FIELD OF ART

The present invention relates to a high molecular material which is a polymer mixture material useful as a medical material, a cosmetic material, a coating material and the like, and a liquid high molecular composition as a starting material thereof, as well as a medical material which is a polymer mixture having both superior biocompatibility and dynamic strength, and a high molecular composition for the medical material as a starting material thereof.

BACKGROUND OF ART

A polymer containing a phosphorylcholine group has a structure similar to that of a phospholipid constituting a cell membrane, and therefore has high biocompatibility, to exhibit superior properties as a medical high molecular material, such as non-activating ability of a complement including blood coagulation factor, lack of biomaterial (including protein and cells) absorbing property, antithrombus property, moisture holding property, and lipid bilayer stabilizing ability (Kazuhiko Ishihara, et.al., Journal of Biomedical Materials Research, 24(1990) 1069–1077, Kazuhiko Ishihara, et.al., Journal of Biomedical Materials Research, 25(1991) 1397–1407).

Development of bio-related materials utilizing these properties has actively been performed. For example, it is described in Japanese Laid-open Patent Application No.91-39309 that a copolymer of 2-methacryloyloxyethylphosphorylcholine and an ester of methacrylic acid is a superior biocompatible material. It is described in WO93/01221 that, when a polymer containing a phosphorylcholine group is utilized as a coating material, the coated article can be used as a material having a biocompatible surface for various bio-related purposes. It is disclosed in WO93/16117 that a water-soluble cellulose derivative produced by graft polymerization of a water-soluble cellulose with 2-methacryloyloxyethylphosphorylcholine has both biocompatibility and affinity with cellulose, and can be used as biocompatible material for, e.g., hemocatharsis. It is disclosed in Japanese Laid-open Patent Application No.84-43342 that a high molecular composition of a moisture sensor material consisting of a polymer having a phosphorylcholine group and a thin film material which is a water-soluble polymer is useful as a moisture sensor material. It is disclosed in Japanese Laid-open PCT application No. 95-504459 that a high molecular composition of a polymer having a phosphorylcholine group and a polymer having desirable mechanical and/or physical properties is suitable for a biomedical material. Various monomers, homopolymers, and copolymers having a phosphorylcholine group, and methods for producing the same are previously known as described in, e.g., Japanese Laid-open Patent Application Nos. 79-63025, 83-154591, 88-222183, 93-107511 and 94-41157, and WO093/01221.

Although a polymer or copolymer having the phosphorylcholine group has significant biocompatibility, mechanical properties such as dynamic strength and durability are not always sufficient, in terms of a medical material. Thus, various studies have been made regarding copolymerizable monomers to be copolymerized with the monomer having a phosphorylcholine group. An attempt to improve dynamic strength and durability by mixing a hydrophobic polymer having such properties has also been made. However, in the case of the polymer having a phosphorylcholine group, which is a functional group exhibiting a uniquely significant water-solubility, sufficiently good result has not yet been obtained unlike the case of conventionally performed mixing of hydrophobic polymers with another hydrophobic polymer.

Alternatively, it is known that a segmented polyurethane is superior in dynamic properties, and has better blood compatibility than other materials (Japanese Laid-open Patent Application No.82-139352, European Patent Specification No.68385, U.S. Pat. No. 4,379,904, WO83/00695). Such segmented polyurethanes are widely used as medical materials such as blood circuits, artificial hearts, various catheters, and medical sensors ("Artificial Organs" Ed. Tetsuzo Agishi, 1994-95, Published by Nakayama Shoten). However, when these materials are used for a long time in an organism, inflammatory response, deterioration of materials caused by cell adhesion, and calcification occur. Therefore ideal antithrombus property is not always obtained, thus not being sufficient.

An attempt to mix two or more sorts of high molecular compounds having different properties to reform the material is called "polymer blend" and is commonly performed. When a film is produced with a mixture of two high molecular compounds having properties in contrast, such as a mixture of a high molecular compound having high hydrophilicity and a high molecular compound having high hydrophobicity, or a mixture of a high molecular compound having a high crysterization property and a high molecular compound having a high non-crysterization property, molecules of high molecular compounds having the same property gather by movement of molecules, to occur phase separation. Reform of materials utilizing the phase separation is also a common method of polymer blend. A multi-phase structure material has been developed utilizing phase separation mechanism of a high molecular mixture system which can be mutually dissolved. However, if high molecular compounds having extremely different hydrophilicity or hydrophobicity are mixed, aggregation or cloudness occurs because of phase separation, thus being not suitable for a biocompatible material for preventing adhesion of cells of the order of micrometers.

For example, in the method for producing a high molecular compound described in the aforementioned Japanese Laid-open PCT Application No.95-504459, 1:2 copolymer of 2-(methacryloyl)oxy-2'-(trimethylammonium)ethyl phosphate and n-dodecyl methacrylate, and segmented polyurethane are dissolved in a single solvent of dichloromethane or a mixed solvent of ethyl acetate and propane-2-ol. However, when the solvents are employed with such combination of high molecular compounds, only a part thereof is dissolved or swelled, and a uniform solution cannot thus be obtained. Therefore, a film obtained by evaporation of the solvent from such an ununiform solution cannot be utilized as a biocompatible material because of aggregation and cloudiness. In the combination of high molecular compounds having extremely different hydrophilicity or hydrophobicity, it is known that a mixture system without cloudiness in macro observation can be obtained as long as the compounds are covalently bonded to form a blocked copolymer. However, such a mixture is not known produced by mere mixing of two high molecular compounds.

DISCLOSURE OF THE PRESENT INVENTION

It is an object of the present invention to provide a high molecular material and a medical material having superior biocompatibility and superior mechanical properties such as dynamic properties and durability.

It is another object of the present invention to provide a liquid high molecular composition for a starting material of the high molecular material and a medical material having a superior biocompatibility and superior mechanical properties such as dynamic properties and durability, which is uniform and stable for long time period.

For achieving the aforementioned object, the present inventors made various studies of hydrophobic monomers, hydrophobic polymers to be mixed, solvents and methods for mixing. As a result, they found out that a phosphorylcholine group-containing copolymer prepared by copolymerization with a hydrophobic monomer can give a uniform solution stable in a long period of time when it is dissolved together with a hydrophobic polymer in a specific solvent, even if the copolymer includes a phosphorylcholine group having extremely high polarity. They also found out that the structure of the high molecular material obtained after evaporation of the solvent shows phase separation in which domains of several hundred micrometers or less in size consisting of the polymer having the phosphorylcholine group are uniformly distributed in a phase consisting of the hydrophobic polymer. They thus completed the present invention.

That is, according to the present invention, there is provided a high molecular material characterized in that the material is a mixed material comprising a copolymer A produced by copolymerization of a monomer composition containing a monomer having a side chain represented by the formula (1)

(wherein $R^1$, $R^2$ and $R^3$ are the same or different groups and stand for a hydrogen atom or an alkyl group having 1 to 4 carbon atoms) and a hydrophobic monomer, and one or more sorts of hydrophobic polymer B other than the copolymer A; wherein the structure of the mixed material shows phase separation in which domains of several hundred micrometers or less in size consisting of the copolymer A are uniformly distributed in a phase consisting of the hydrophobic polymer B.

According to the present invention, there is also provided a liquid high molecular composition as a starting material of the high molecular material containing as the hydrophobic polymer B a segmented polyurethane selected from the group consisting of a segmented polyurethane obtained by polyaddition of dicyclohexylmethane diisocyanate and polyether diol, a segmented polyurethane obtained by polyaddition of diphenylmethane diisocyanate and polyether diol, and mixtures thereof, the liquid high molecular composition comprising a copolymer A produced by copolymerization of a monomer composition containing a monomer having a side chain represented by the formula (1) and a hydrophobic monomer; one or more sorts of hydrophobic polymer B other than the copolymer A containing a segmented polyurethane selected from the group consisting of a segmented polyurethane obtained by polyaddition of dicyclohexylmethane diisocyanate and polyether diol, a segmented polyurethane obtained by polyaddition of diphenylmethane diisocyanate and polyether diol, and mixtures thereof; and a mixed solvent consisting of a halogenated hydrocarbon solvent and a lower alcohol solvent, the liquid high molecular composition having turbidity of 60% or less.

According to the present invention, there is further provided a medical material characterized in that the medical material is a mixed material comprising a copolymer A produced by copolymerization of a monomer composition containing a (meth)acrylate of an alkyl alcohol having 1 to 4 carbon atoms having a side chain represented by the formula (1), and a hydrophobic monomer selected from the group consisting of a (meth) acrylate of a branched alkyl alcohol having 5 to 15 carbon atoms, an alicyclic alkyl (meth)acrylate, and mixtures thereof; and one or more sorts of hydrophobic polymer B other than the copolymer A, the mixed material containing as the hydrophobic polymer B a segmented polyurethane obtained by polyaddition of dicyclohexylmethane diisocyanate and polyether diol, the structure of the mixed material showing phase separation in which domains of several hundred micrometers or less in size consisting of the copolymer A are uniformly distributed in a phase consisting of the hydrophobic polymer B.

According to the present invention, there is further provided a liquid high molecular composition as a starting material of the medical material, comprising a copolymer A produced by copolymerization of a monomer composition containing a (meth)acrylate of an alkyl alcohol having 1 to 4 carbon atoms having a side chain represented by the formula (1), and a hydrophobic monomer selected from the group consisting of a (meth) acrylate of a branched alkyl alcohol having 5 to 15 carbon atoms, an alicyclic alkyl (meth)acrylate, and mixtures thereof; one or more sorts of hydrophobic polymer B other than the copolymer A containing a segmented polyurethane obtained by polyaddition of dicyclohexylmethane diisocyanate and polyether diol; and a mixed solvent consisting of a halogenated hydrocarbon solvent and a lower alcohol solvent, the liquid high molecular composition having turbidity of 60% or less.

According to the present invention, there is further provided a medical material characterized in that the medical material is a mixed material comprising a copolymer A produced by copolymerization of a monomer composition containing a (meth)acrylate of an alkyl alcohol having 1 to 4 carbon atoms having a side chain represented by the formula (1), and as a hydrophobic monomer an alkyl (meth) acrylate having a urethane bond; and one or more sorts of hydrophobic polymer B other than the copolymer A, wherein the mixed material contains as the hydrophobic polymer B a segmented polyurethane obtained by polyaddition of diphenylmethane diisocyanate and polyether diol, and wherein the structure of the mixed material shows phase separation in which domains of several hundred micrometers or less in size consisting of the copolymer A are uniformly distributed in a phase consisting of the hydrophobic polymer B.

According to the present invention, there is further provided a liquid high molecular composition as a starting material of the medical material, comprising a copolymer A produced by copolymerization of a monomer composition containing a (meth)acrylate of an alkyl alcohol having 1 to 4 carbon atoms having a side chain represented by the formula (1), and as a hydrophobic monomer an alkyl (meth) acrylate having an urethane bond; one or more sorts of hydrophobic polymer B other than the copolymer A containing a segmented polyurethane obtained by polyaddition of diphenylmethane diisocyanate and polyether diol; and a mixed solvent consisting of a halogenated hydrocarbon solvent and a lower alcohol solvent, the liquid high molecular composition having turbidity of 60% or less.

BEST MODE FOR CARRYING OUT THE PRESENT INVENTION

The present invention will be explained more in detail hereinbelow.

The high molecular material and medical material of the present invention are a mixed material containing as a composition a specific copolymer A produced by copolymerization of a monomer composition containing a monomer having a specific side chain and a hydrophobic monomer; and one or more sorts of hydrophobic polymer B other than the copolymer A, wherein the structure of the mixed material shows phase separation in which domains consisting of the copolymer A of several hundred micrometers or less, preferably 100 micrometers or less, and more preferably 0.01 to 50 micrometers in size are uniformly distributed in a phase consisting of the hydrophobic polymer B. As used herein, the uniformly distributed phase separation means that the copolymer A and the hydrophobic polymer B show phase separation, and the domains of the copolymer A in a specific size are scattered in the phase of the hydrophobic polymer B so that this mixed material effectively and simultaneously exhibits physical properties such as mechanical strength which the hydrophobic polymer B has and biocompatibility which the copolymer A has.

The liquid high molecular composition of the present invention can be a starting material of such a high molecular material and a medical material. A polymer having a phosphorylcholine group has hitherto been used only with solvents having extremely high water-solubility such as water and lower alcohols because of its extremely high hydrophilicity. However, in the present invention, for preparing a mixed solution of the polymer having a phosphorylcholine group with a hydrophobic polymer, a specific combination of the copolymer A and the hydrophobic polymer B is selected, and specific solvents are also selected, to give uniform liquid state which enables production of the high molecular material and the medical material of the present invention. As used herein, uniform liquid state means that the copolymer A and the hydrophobic polymer B show compatibility to the extent that the mixture has such uniformity as to show the turbidity (the percentage measured with the definition that the state of complete light shielding is 100 and a cell filled only with the solvent (or an empty cell, if the sample is fused without solvent) is zero) of not more than 60%, and preferably not more than 50%. Therefore, such liquid high molecular composition can be stored for a long period of time without separation, even if stored in the liquid state. The starting mateiral of the high molecular material of the present invention, other than those defined as the liquid high molecular composition of the present invention, may also be in the aforementioned uniform liquid state. For example, such starting material may suitably be prepared by selecting the combination of copolymer A and hydrophobic polymer B. The sorts of the solvents may also be suitably selected, or the solvents may be omitted if the polymers are in the fused state.

In summary, the present invention is to solve the difficulty to obtain the uniform liquid state of the (co)polymer having a phosphorylcholine group and other polymers because of the extreme hydrophilicity of the phosphorylcholine group. In addition, it is found out that, by removing solvents from the starting material in such uniform liquid state or by drying such starting material, a mixed material in solid state is obtained which is novel in terms of aforementioned specific structure and has both mechanical strength and biocompatibility. The reason the aforementioned specific construction is formed by drying the liquid high molecular composition of the present invention to vaporize the solvent is supposed as follows: in the course of solidification, it becomes difficult for the copolymer A having a phosphorylcholine group having extremely high water solubility to maintain uniformly dissolved state in hydrophobic circumstance in hydrophobic polymer B, and therefore the copolymer A gradually gathers, which results in phase separation similar to W/O emulsification, to stabilize the system.

The monomer having the specific side chain as a requisite component in the monomer composition for preparing the copolymer A is a monomer having a side chain represented by the formula (1)

wherein $R^1$, $R^2$ and $R^3$ may be the same or different groups and stand for a hydrogen atom or an alkyl group having 1 to 4 carbon atoms. This monomer has a polymerizable double bond and a side chain represented by the formula (1) in the molecule thereof, and may include 2-(methacryloyloxy) ethyl-2'-(trimethylammonio)ethyl phosphate, 3-(methacryloyloxy)propyl-2'-(trimethylammonio)ethyl phosphate, 4-(methacryloyloxy)butyl-2'-(trimethylammonio)ethyl phosphate, 5-(methacryloyloxy) pentyl-2'-(trimethylammonio)ethyl phosphate, 6-(methacryloyloxy)hexyl-2'-(trimethylammonio)ethyl phosphate, 2-(methacryloyloxy)ethyl-2'-(triethylammonio) ethyl phosphate, 2-(methacryloyloxy)ethyl-2'-tripropylammonio)ethyl phosphate, 2-(methacryloyloxy) ethyl-2'-(tributylammonio)ethyl phosphate, 2-(acryloyloxy) ethyl-2'-(trimethylammonio)ethyl phosphate, 2-(acryloyloxy)ethyl-2'-(trimethylammonio)ethyl phosphate, 2-(methacryloyloxy)propyl-2'-(trimethylammonio)ethyl phosphate, 2-(methacryloyloxy) butyl-2'-(trimethylammonio)ethyl phosphate, 2-(methacryloyloxy)pentyl-2'-(trimethylammonio) ethylphosphate, 2-(methacryloyloxy)hexyl-2'-(trimethylammonio)ethyl phosphate, 2-(vinyloxy)ethyl-2-(trimethylammonio)ethyl phosphate, 2-(allyloxy)ethyl-2'-(trimethylammonio)ethyl phosphate, 2-(p-vinylbenzyloxy) ethyl-2'-(trimethylammonio)ethyl phosphate, 2-(p-vinylbenzoyloxy)ethyl-2'-(trimethylammonio)ethyl phosphate, 2-(styryloxy)ethyl-2'-(trimethylammonio)ethyl phosphate, 2-(p-vinylbenzyl)ethyl-2'-(trimethylammonio) ethyl phosphate, 2-(vinyloxycarbonyl)ethyl-2'-(trimethylammonio)ethyl phosphate, 2-(allyloxycarbonyl) ethyl-2'-(trimethylammonio)ethyl phosphate, 2-(acryloylamino)ethyl- 2'-(trimethylammonio)ethyl phosphate, 2-(vinylcarbonylamino)ethyl-2'-(trimethylammonio)ethyl phosphate, 2-(allyloxycarbonylamino)ethyl-2'-(trimethylammonio) ethyl phosphate, 2-(butenoyloxy)ethyl-2'-(trimethylammonio)ethyl phosphate, 2-(crotonoyloxy)ethyl- 2'-trimethylammonio)ethyl phosphate, ethyl 2'-trimethylammonioethylphosphorylethyl fumarate, butyl 2'-trimethylammonioethylphosphorylethyl fumarate, hydroxyethyl 2'-trimethylammonioethylphosphorylethyl fumarate, ethyl 2'-triethylammonioehtylphosphorylethl fumarate, butyl 2'-trimethylammonioethylphosphorylethyl fumarate, and hydroxyethyl 2'-trimethylammonioethylphosphorylethyl fumarate. Particularly, for the medical material and the liquid high molecular composition as the starting material therefor, a (meth)acrylate of an alkyl alcohol having 1 to 4 carbon atoms having the side chain represented by the formula (1) is employed. Examples thereof may be selected from the enumeration above.

In the copolymer A, it is desirable that the content of the monomer having side chain represented by the formula (1) is at least 1 mol % or more, preferably 10 mol % or more, most preferably 10 to 70 mol %, in order to give sufficient biocompatibility to the obtained material.

The hydrophobic monomer as a requisite component of the monomer composition for preparing the copolymer A shows such effect as increasing compatibility with hydrophobic polymer B which will be explained later, upon preparing the starting material of the high molecular material. The hydrophobic monomer has low solubility in water, and is copolymerizable with the monomer having the side chain of the formula (1). Specifically, it may include styrene and its derivatives such as methylstyrene and chloromethylstyrene; linear alkyl (meth)acrylates such as methyl (meth)acrylate, ethyl (meth)acrylate, butyl (meth)acrylate and dodecyl (meth)acrylate; alicyclic alkyl (meth)acrylates such as cyclohexyl (meth)acrylate; (meth)acrylates of a branched alkyl alcohol having 5 to 15 carbon atoms such as 2-ethylhexyl (meth)acrylate; alkyl (meth)acrylates having a reactive functional group such as glycidyl (meth)acrylate and (meth)acryloyloxyethyltrimethoxysilane; alkyl (meth)acrylates having an urethane bond such as 2-(meth)acryloyloxyethylbutyl carbamate, 2-(meth)acryloyloxyethylbenzyl carbamate and 2-(meth)acryloyloxyethylphenyl carbamate; ethyl vinyl ether, butyl vinyl ether, vinyl acetate, vinyl chloride, vinylidene chloride, ethylene, propylene, isobutylene, diethyl fumarate, and diethyl maleate. Particularly, for the medical material and the liquid high molecular composition as the starting material therefor, a hydrophobic monomer selected from the group consisting of (meth)acrylates of a branched alkyl alcohol having 5 to 15 carbon atoms, alicyclic alkyl (meth)acrylate andmixtures thereof, or an alkyl (meth)acrylate having an urethane bond is employed, depending on the hydrophobic polymer B which will be explained later.

In the copolymer A, the content of the unit of the hydrophobic monomer is preferably 30 to 90 mol %.

The combination of the monomer having the side chain represented by the formula (1) and the hydrophobic monomer is preferably the combination resulting in random and uniform distribution of the units of each monomer in the copolymer A so that the copolymer A and the hydrophobic polymer B which will be explained later form a uniform liquid state. For example, the combination of (meth) acrylates which have high polymerizability and can be controlled easily is optimal.

The monomer composition for preparing the copolymer A may include another monomer which is polymerizable with the monomer having the side chain represented by the formula (1), as a comonomer other than the aforementioned requisite components, such as water-soluble monomers such as (meth)acrylic acid, (meth)acrylic amide, 2-hydroxyethyl (meth)acrylate and N-vinylpyrrolidone. The content of such monomer unit is preferably 10 mol% or less of the copolymer A.

The copolymer A may be prepared using a polymerization initiator according to usual polymerization methods such as solution polymerization, suspension polymerization, emulsion polymerization or mass polymerization. The molecular weight of the copolymer A is preferably in a range of 3000 to 700000 in terms of number average molecular weight, and more preferably in a range of 5000 to 400000 considering the properties as the high molecular compound and the solubility to the solvent.

Specific examples of the copolymer A may include a copolymer of 2-(methacryloyloxy)ethyl-2'-(trimethylammonio)ethyl phosphate and cyclohexyl methacrylate, a copolymer of 2-(methacryloyloxy)ethyl-2'-(trimethylammonio)ethyl phosphate and 2-ethylhexyl methacrylate, a copolymer of 2-(methacryloyloxy)ethyl-2'-(trimethylammonio)ethyl phosphate and n-butyl methacrylate, a copolymer of 2-(methacryloyloxy)ethyl-2'-(trimethylammonio)ethyl phosphate and n-dodecyl methacrylate, a copolymer of 2-(methacryloyloxy)ethyl-2'-(trimethylammonio)ethyl phosphate and styrene, a copolymer of 2-(butenoyloxy)ethyl-2'-(trimethylammonio) ethyl phosphate and propylene, a copolymer of 2-(crotonoyloxy)ethyl-2'-trimethylammonio)ethyl phosphate and diethyl fumarate, a copolymer of 2-(methacryloyloxy)ethyl-2'-(trimethylammonio)ethyl phosphate, butyl methacrylate and 2-methacryloyloxyethylphenyl carbamate, a copolymer of 2-(methacryloyloxy)ethyl-2'-(trimethylammonio)ethyl phosphate, 2-ethylhexyl methacrylate and 2-methacryloyloxyethyltrimethoxysilane.

The copolymer A for the medical material of the present invention is a copolymer produced by copolymerization of a monomer composition containing a (meth)acrylate of an alkyl alcohol having 1 to 4 carbon atoms having a side chain represented by the formula (1), and a hydrophobic monomer selected from the group consisting of (meth)acrylate of a branched alkyl alcohol having 5 to 15 carbon atoms, an alicyclic alkyl (meth)acrylate, and mixtures thereof; or a copolymer produced by copolymerization of a monomer composition containing an (meth)acrylate of an alkyl alcohol having 1 to 4 carbon atoms having a side chain represented by the formula (1), and as a hydrophobic monomer an alkyl (meth) acrylate having an urethane bond. Examples of these may be the appropriate ones in the aforementioned examples of the copolymer A of the high molecular material.

The hydrophobic polymer B for the high molecular material and the starting material thereof has very low solubility to water, and can give mechanical properties such as dynamic strength and durability to the resulting high molecular material. In addition, when the hydrophobic polymer B is mixed with the copolymer A, a liquid high molecular composition of the aforementioned uniform liquid state is obtained, and when the mixture is solidified as the material, the aforementioned specific structure can be formed. Specifically, the hydrophobic polymer B may include high molecular materials such as segmented polyurethane, polyvinyl chloride, polypropylene, polystyrene, polyethylene, ABS resin, polymethylpentene, styrene-butadiene block copolymer, polymethyl methacrylate, polydimethylsiloxane, polyethylene terephthalate, polyallylsulfone, polysulfone, polyether imide, polycarbonate, polybutylene terephthalate, polyacetal, nylon, nylon-ABS resin copolymer, polysulfone-thermal plastic polyester copolymer, polytetrafluoroethylene, cellulose, natural rubber and collagen; high molecular materials for medical material such as those containing immobilized bioactive substances, such as materials which contain immobilized heparin or which release heparin in controlled manner, and materials which contain immobilized prostaglandin or which release prostaglandin in controlled manner. The molecular weight of the hydrophobic polymer B is, considering the properties as the high molecular compound and solubility to the solvent, preferably in a range of 3000 to 700000 in terms of number average molecular weight, but not limited thereto.

Particularly, by employing segmented polyurethane as the hydrophobic polymer B, a material having both superior biocompatibility and practical physical properties for medical materials, such as blood circuits, artificial hearts, various catheters, medical sensors and equipments for cell culturing, may be obtained.

The segmented polyurethane is a group of polymers obtained by polyaddition of excess amount of diisocyanates or polyisocyanates with diols including polyethers and polyesters, followed by polyaddition with diols or diamines as a chain extending agent. The isocyanates may include diphenylmethane diisocyanate and dicyclohexane diisocyanate, and the diols may include polyester diol and polyether diol. The chain extending agent may include ethylenediamine, 4,4'-methylene dianiline, water, propylenediamine, butane diol. Also, "Biomer" (produced by Ethicon Inc.), "TM Series" (produced by Toyobo Co., Ltd.), "Pellethane" (produced by Upjohn Chem. Co.), "Angioflex" (produced by Abiomed Inc.) "Cardiothane" (produced by Kontron) are polyaddition products of diphenylmethane diisocyanate and polyoxytetramethylene glycol, and various chain extending agent is used for producing these products. "Tecoflex" (produced by Thermo Elec. Corp.) is a polyaddition product of dicyclohexylmethane diisocyanate and polyoxymethylene glycol. These commercially available products may also be employed.

As the hydrophobic polymer B for the medical material and the liquid high molecular composition as the starting material thereof of the present invention, a segmented polyurethane obtained by polyaddition of dicyclohexylmethane diisocyanate and polyether diol is employed, when the copolymer A is a copolymer produced by copolymerization of a monomer composition containing a (meth)acrylate of an alkyl alcohol having 1 to 4 carbon atoms having the side chain represented by the formula (1), and a hydrophobic monomer selected from the group consisting of a (meth) acrylate of a branched alkyl alcohol having 5 to 15 carbon atoms, an alicyclic alkyl (meth)acrylate and mixtures thereof. On the other hand, a segmented polyurethane obtained by polyaddition of diphenylmethane diisocyanate and polyether diol is employed when the copolymer A is a copolymer produced by copolymerization of a monomer composition containing a (meth)acrylate of an alkyl alcohol having 1 to 4 carbon atoms having the side chain represented by the formula (1), and as a hydrophobic monomer an alkyl (meth)acrylate having a urethane bond. Examples of these may be the appropriate ones in the aforementioned examples of the hydrophobic polymer B.

In the high molecular material, the medical material and the liquid high molecular composition as the starting material thereof of the present invention, the ratio of the copolymer A and the hydrophobic polymer B is preferably in ranges of 0.5 to 95 wt % of the copolymer A and 99.5 to 5 wt % of the hydrophobic polymer B, particularly in ranges of 1 to 30 wt % of the copolymer A and 99 to 70wt % of the hydrophobic polymer B, with respect to the total amount of the copolymer A and the hydrophobic polymer B. If the content of the copolymer A is less than 0.5 wt %, the biocompatibility due to the side chain represented by the formula (1) tends to be difficult to emerge, and if the content of the copolymer A exceeds 95 wt %, dynamic strength and durability due to the hydrophobic polymer B tends to be difficult to emerge, thus not being preferable.

The high molecular material of the present invention may be obtained by preparing a mixture of the copolymer A and one or more sorts of the hydrophobic polymer B other than the copolymer A in the uniform liquid state (either dissolved in solvents or fused by heating), followed by converting the mixture into the solid state in desired form by cooling or vaporizing of the solvent. By appropriately selecting the hydrophobic monomer constituting the copolymer A so that the copolymer A becomes compatible with the hydrophobic polymer B, the copolymer A having the phosphorylcholine group having extremely high polarity interacts and gathers strongly in the hydrophobic environment in the process of cooling and solidifying, resulting in a material showing the specific phase separation. Particularly, it is preferable to form liquid state by selecting the solvent appropriately. It is a matter of course that the solvent to be employed has compatibility with each polymer. The solvent is preferably a low molecular compound which can easily be removed by evaporation for ready coating or filming. The solvent may be a mixed solvent. The solvent may include without limitation halogenated hydrocarbon solvents such as dichloromethane, chloroform and 1,2-dichloroethane; lower alcohols such as methanol, ethanol, n-propanol and propane-2-ol; ethyl acetate and tetrahydrofuran. The solvent having good compatibility may be selected by searching for an optimal combination by which the solubility parameter of the polymers constituting the high molecular material approximates the solubility parameter of the solvent.

In the case of the specific high molecular material of the present invention, i.e., the high molecular material which is a mixed material containing the copolymer A of the monomer having the side chain represented by the formula (1) and the hydrophobic monomer, and one or more sorts of the hydrophobic polymer B other than the copolymer A containing a segmented polyurethane selected from the group consisting of a segmented polyurethane obtained by polyaddition of dicyclohexylmethane diisocyanate and polyether diol, a segmented polyurethane obtained by polyaddition of diphenylmethane diisocyanate and polyether diol and mixtures thereof, or the liquid high molecular composition as the starting material of the medical material of the present invention, a mixed solvent consisting of the halogenated hydrocarbon solvent and the lower alcohol solvent may be used as the solvent to keep the specific copolymer A and the specific hydrophobic polymer B in the aforementioned uniform liquid state. Such mixed solvent preferably has SP value (solubility parameter of the solvent($10^{-3}J^{1/2}m^{-3/2}$) of 20 to 24. For example, mixed solvents of chloroform/methanol, chloroform/ethanol, dichloromethane/methanol or dichloromethane/ethanol in the volume ratio in a range of 8/2 to 6/4 are appropriate, but not limited thereto. Selection of such optimal solvent is explained below with the example of selecting the optimal solvent for the polymer of 2-(methacryloyloxy)ethyl-2'-(trimethylammonium)ethyl phosphate (abbreviated as MPC hereinbelow) and the segmented polyurethane ("Tecoflex" produced by Thermo Elec. Corp.).

First, the solubility when 1 mg of each polymer enumerated in Table 1 is dissolved in 1 ml of various solvents is shown in Table 1.

TABLE 1

| | Type of Solvent (SP value) | | | | | |
|---|---|---|---|---|---|---|
| Polymer | Water (47.1) | Methanol (29.7) | Ethanol (26.0) | Dichloro methane (19.8) | Tetrahydro furan (18.6) | Dichloromethane/ ethanol (7/3 in volume ratio) (21.7) |
| Poly MPC | ++ | ++ | ++ | − | − | − |
| PMC | ± | + | ++ | ± | + | ++ |
| PME | ± | + | ++ | ± | + | ++ |
| SPU-1 | − | − | − | ++ | ++ | ++ |

Poly MPC: homopolymer of MPC
PMC: copolymer of MPC (29.5 mol %) and cyclohexyl methacrylate
PME: copolymer of MPC (27.0 mol %) and 2-ethylhexyl methacrylate
SPU-1: segmented polyurethane
Solubility: (++) dissolved, (+) dissolved after five minutes of ultrasonic irradiation, (±) swelled, (−) not dissolved As seen from Table 1, MPC homopolymer is dissolved only in water and alcohols because of its extremely high polarity, while PMC and PME, which are copolymers of a hydrophobic monomer and MPC, can be dissolved in or swelled by dichloromethane or tetrahydrofuran with irradiation of ultrasonic wave. On the other hand, the segmented polyurethane can be dissolved in dichloromethane or tetrahydrofuran, although not dissolved in water or alcohols. Further, solubility of each polymer in a mixed solvent of dichloromethane and ethanol was examined, and it was found out that polymers other than MPC homopolymer were dissolved easily. As a result it is seen that, by selecting PMC or PME as the MPC polymer and employing the mixed solvent of dichloromethane and ethanol, the mixture of these can be in the aforementioned uniform liquid state.

When forming the uniform liquid state, by irradiating ultrasonic wave, uniformity may be further increased, which results in the smaller size of the domains consisting of the copolymer A formed upon converting the liquid into the material (solid state) and results in further uniformity of the distribution of the domains. For irradiation of the ultrasonic wave, an ultrasonic oscillator of probe type, or a commercially available ultrasonic washer may be employed. The irradiation time is preferably not less than 5 minutes. Alternatively, the mixture of polymers in the solid state may be fused under heat without any solvent, employing a commonly used machine such as a kneader, a banbury mixer, a roll or various molding machines. The mixture may be fused so that the turbidity thereof becomes 60% or less, and preferably 50% or less.

In the liquid high molecular composition of the present invention, the amount of the solvent is not limited and is suitably selected provided that the copolymer A and the hydrophobic polymer B can be dissolved to form the aforementioned uniform liquid state.

The high molecular material and the medical material of the present invention can give desirable function to various materials by molding the uniform liquid such as the liquid high molecular composition of the present invention with the desirable materials, or by coating the liquid on the surface of the desired materials. Upon coating on the surface of the material, by selecting as the hydrophobic polymer B a high molecular material which has similar structure to the material, adhesion and durability may be significantly increased.

The high molecular material of the present invention is superior in physical properties such as biocompatibility and dynamic strength, and therefore may be utilized widely for medical materials and coating materials such as blood circuits, artificial hearts, various catheters, medical sensors and equipments for cell culturing.

Since the high molecular material of the present invention has in the specific structure the copolymer A produced by copolymerization of the monomer composition containing the monomer having the side chain represented by the formula (1) and the hydrophobic monomer, and the hydrophobic polymer B other than the copolymer A, it has both superior biocompatibility caused by the monomer having the side chain represented by the formula (1), and physical properties such as practical mechanical strength caused by the hydrophobic polymer B. In addition, since the material of the present invention shows phase separation in which the domains consisting of the copolymer A in the specific size is uniformly distributed in the phase consisting of the hydrophobic polymer B, it is useful as a medical material having both biocompatibility and mechanical properties. By employing the segmented polyurethane as the hydrophobic polymer B, the material of the present invention is free from problems of peeling caused by lack of adhesion with the base material even in the cases in which durability is particularly required or in which the material is used as a medical material for blood circulation system which requires the material to have flexibility and which tends to be subjected to physical transformation. Therefore, the material of the present invention is useful for various medical materials such as blood circuits, artificial hearts, various catheters, medical sensors and equipments for cell culturing.

EXAMPLES

The present invention will be explained with reference to Synthesis Examples, Examples, and Comparative Examples hereinbelow, but the present invention is not limited thereto.

Synthesis Examples 1 to 5

In a mixed solvent of $CH_2Cl_2/C_2H_5OH$ (7/3 in weight ratio), cyclohexyl methacrylate (abbreviated as CHMA hereinbelow), 2-ethylhexyl methacrylate (abbreviated as EHMA hereinbelow), or a monomer composition of MPC and CHMA or EHMA (30/70 in mole %) was dissolved in the concentration of 1 mol/liter. In each of the obtained solution, azobisisobutylonitrile as a polymerization initiator was dissolved in the concentration of 5 mmol/liter, and each of the resulting solution was subjected to solution polymerization at 60° C. for a time period shown in Table 2.

After the completion of the reaction, each of the reaction liquid was dripped into ether to precipitate the polymer. The precipitated polymer was then separated by filtration, and residual monomers therein were removed. The obtained polymer was dried under reduced pressure, and the yield of the polymer was determined by measuring the weight. The results are shown in Table 2 under Synthesis Examples 1 to 4. In Synthesis Examples 1 and 2, homopolymers of CHMA and EHMA (abbreviated as PC and PE, respectively) were prepared, respectively. The copolymers prepared in Synthesis Examples 3 and 4 were identified by IR spectrum. As a result, the disappearance of a carbon-carbon double bond was confirmed by the absence of a peak around 1600 $cm^{-1}$; the presence of a phosphorylcholine group was confirmed by a peak around 1200 $cm^{-1}$ due to $N^+$ $(CH_3)_3$ and a peak of P—O—$CH_2$ bond at 1400 $cm^{-1}$; the presence of an ester group was confirmed by a peak of C=O bond at 1730 $cm^{-1}$; the presence of an alkyl group was confirmed by peaks of —$CH_2$— and —$CH_3$ around 2800–3000 $cm^{-1}$; and the presence of a cyclohexyl group was confirmed by a peak of cyclic ring at 1050 $cm^{-1}$. Accordingly, it was confirmed that a copolymer of MPC and CHMA (abbreviated as PMC hereinbelow) was obtained in Synthesis Example 3, and that a copolymer of MPC and EHMA (abbreviated as PME hereinbelow) was obtained in Synthesis Example 4).

Further, in Synthesis Example 5, a monomer composition composed of three components, namely MPC/EHMA/2-methacryloyloxyethyltrimethoxysilane (abbreviated as MTSi hereinbelow) in the ratio of 30:69:1 by mole % was polymerized in the same way as in Synthesis Example 4 to obtain a copolymer of MPC, EHMA, and MTSi (abbreviated as PMESi hereinbelow). The yield of the polymer is shown in Table 2.

Synthesis Example 6

In a mixed solvent of $CH_2Cl_2/C_2H_5OH$ (7/3 in weight ratio), a monomer composition of MPC and n-dodecyl methacrylate (abbreviated as DMA hereinbelow) (33/67 in mole %) was dissolved in the concentration of 1 mol/liter. In the obtained solution was dissolved azobisisobutyronitrile as a polymerization initiator in the concentration of 5 mmol/liter, and the resulting solution was subjected to solution polymerization at 60° C. for a time period shown in Table 2.

After the completion of the reaction, the reaction liquid was dripped into ether to precipitate the copolymer. The precipitated copolymer was then separated by filtration and residual monomers therein were removed. The obtained copolymer was dried under reduced pressure, and the yield of the copolymer was determined by measuring the weight. The results were shown in Table 2 under Synthesis Example 6. The copolymer was identified by IR spectrum. As a result, the disappearance of the carbon-carbon double bond was confirmed by the absence of a peak around 1600 $cm^{-1}$; the presence of a phosphorylcholine group was confirmed by a peak around 1200 $cm^{-1}$ due to $N^+$ $(CH_3)_3$ and a peak of P—O—$CH_2$ bond at 1400 $cm^{-1}$; the presence of an ester group was confirmed by a peak of C=O bond at 1730 $cm^{-1}$; and the presence of an alkyl group was confirmed by peaks of —$CH_2$— and —$CH_3$ around 2800–3000 $cm^{-1}$. Accordingly, it was confirmed that a copolymer of MPC and DMA (abbreviated as PMD hereinbelow) was obtained in Synthesis Example 6.

Synthesis Example 7

In a mixed solvent of $CH_2Cl_2/C_2H_5OH$ (7/3 in weight ratio), a monomer composition of MPC, N-butyl methacrylate (abbreviated as BMA hereinbelow), and 2-methacryloyloxyethylphenylurethane (abbreviated as MBPU hereinbelow) (30/60/10 in mole %) was dissolved in the concentration of 1 mol/liter. In the obtained solution was dissolved azobisisobutyronitrile as a polymerization initiator in the concentration of 5 mmol/liter, and the resulting solution was subjected to solution polymerization at 60° C. for a time period shown in Table 2.

After the completion of the reaction, the reaction liquid was dripped into ether to precipitate the copolymer. The precipitated copolymer was then separated by filtration, and residual monomers therein were removed. The obtained copolymer was dried under reduced pressure, and the yield of the copolymer was determined by measuring the weight. The results are shown in Table 2 under Synthesis Example 7. The copolymer was identified by IR spectrum. As a result, the disappearance of the carbon-carbon double bond was confirmed by the absence of a peak around 1600 $cm^{-1}$; the presence of a phosphorylcholine group was confirmed by a peak around 1200 $cm^{-1}$ due to $N^+$ $(CH_3)_3$ and a peak of P—O—$CH_2$ bond at 1400 $cm^{-1}$; the presence of an ester group was confirmed by a peak of C=O bond at 1730 $cm^{-1}$; the presence of an alkyl group was confirmed by peaks of —$CH_2$— and —$CH_3$ around 2800–3000 $cm^{-1}$; and the presence of a urethane bond was confirmed by a peak of —NHCOO— group at 1580 $cm^{-1}$. Accordingly, it was confirmed that a copolymer of MPC, BMA, and MBPU (abbreviated as PMU hereinbelow) was obtained in Synthesis Example 7.

[Measurement of Molecular Weight of Copolymer]

The number average molecular weight (Mn) of the obtained copolymer was measured by GPC apparatus manufactured by TOSOH CORPORATION connected to "Asahipak GS-510 column" (trade name) in the mixed solvent of chloroform/ethanol=8/2 in terms of polystyrene as the standard reference material. The results are shown in Table 2.

[Determination of Content of MPC in Copolymer]

6 mg of each MPC-containing copolymer obtained in Synthesis Examples 3 to 7 was dissolved in 10 ml of ethanol, and 50 $\mu$l of the resulting solution was dried at 75° C. until it was solidified. To each of the resulting solidified bodies was added 260 $\mu$l of 70 weight % perchloric acid, and heated at 180° C. for 20 minutes, thereby decomposing the organic phosphorus into inorganic phosphorus. After each of the reactants was cooled, 1.9 ml of distilled water, 0.4 ml of 1.25 weight % ammonium molybdate, and 0.4 ml of 5.0 weight % ascorbic acid were added to each of the reactants, and heated at 100° C. for 5 minutes for coloration. The absorbency of each solution at 817.8 nm was measured to determine the concentration of phosphorus quantitatively. Alternatively, the calibration curve was obtained using disodium hydrogenphosphate. The composition of each copolymer was calculated from the amount of the copolymer used (6 mg), the concentration of phosphorus, and the molecular weight of MPC as a unit. The results are shown in Table 2.

TABLE 2

| Synthesis Example | Copolymer | Polymerization Time (Hour) | MPC Copolymer (yield %) | Molecular Weight Mn | Content of MPC Unit in Copolymer (mole %) |
|---|---|---|---|---|---|
| 1 | only CHMA | 5.5 | PC (75.3) | 315000 | 0 |
| 2 | only EHMA | 5.5 | PE (72.5) | 390000 | 0 |
| 3 | CHMA | 5.5 | PMC (76.7) | 200000 | 29.5 |
| 4 | EHMA | 2.0 | PME (41.0) | 350000 | 27.0 |

TABLE 2-continued

| Synthesis Example | Copolymer | Polymerization Time (Hour) | MPC Copolymer (yield %) | Molecular Weight Mn | Content of MPC Unit in Copolymer (mole %) |
|---|---|---|---|---|---|
| 5 | EHMA + MTSi | 2.0 | PMESi (42.5) | 325000 | 28.5 |
| 6 | DMA | 5.5 | PMD (85.0) | 388000 | 32.5 |
| 7 | BMA + MBPU | 4.0 | PMU (56.0) | 130000 | 30.0 |

Example 1-1 to 1-7

In a solvent prepared by mixing dichloromethane and ethanol in the volume ratio of 7:3, segmented polyurethane (trade name "Tecoflex 60", manufactured by Thermedics CORPORATION, abbreviated as SPU-1 hereinbelow) obtained by polyaddition reaaction of dicyclohexylmethane-diisocyanate and polyoxytetramethylene glycol, PMC (Synthesis Example 3), PME (Synthesis Example 4), PMESi (Synthesis Example 5), or PMD (Synthesis Example 6) was separately dissolved to prepare 5 weight % solutions. Then, SPU-1 solutionandpMC solution, SPU-1 solution and PME solution, SPU-1 solution and PMESi solution, and SPU-1 solution and PMD solution were respectively mixed in the weight ratio of 95:5 and 9:1, respectively, and stirred for 30 minutes to prepare homogeneous solutions. The turbidity of the solutions was determined in the method to be described later.

Subsequently, 26.5 g of each solution was poured into a Teflon dish of the diameter of 75 mm, heated in a drier at 60° C. over night to remove the solvents, and further dried under reduced pressure to form polymer films. The compositions of the films are shown in Table 3 under Examples 1-1 to 1-7. The films were subjected to the measurements to be described later.

Examples 1-8 and 1-9

In a solvent prepared by mixing dichloromethane and ethanol in the volume ratio of 7:3, segmented polyurethane (trade name "Pellethane 2363-90", manufactured by Upjohn Chem. Co., abbreviated as SPU-2 hereinbelow) obtained by polyaddition reaction of diphenylmethanediisocyanate and polyoxytetramethylene glycol, or PMU (Synthesis Example 7) was separately dissolved to prepare 5 weight % solutions. Then, the SPU-2 solution and the PMU solution were mixed in the weight ratio of 95:5 and 9:1, and stirred for 30 minutes to prepare homogeneous solutions. The turbidity of the solutions was determined in the method to be described later.

Subsequently, 26.5 g of each solution was poured into a Teflon dish of the diameter of 75 mm, heated in a drier at 60° C. over night to remove the solvents, and further dried under reduced pressure to form polymer films. The compositions of the films are shown in Table 3 under Examples 1-8 and 9. The films were subjected to the measurements to be described later.

Comparative Examples 1-1 to 1-6

Films of the polymer compositions disclosed in Japanese Laid-open Patent Application No. 7-504459 were prepared, using PMC (Synthesis Example 3), PME (Synthesis Example 4), PMESi (Synthesis Example 5) and PMD (Synthesis Example 6) as copolymer A, respectively. That is, 2.5 g of each copolymer A was mixed with 7.5 g of SPU-1 and 100 g of dichloromethane, and the turbidity of each resulting solution was measured in the method to be described later. Here, it was confirmed by visual observation that SPU-1 was merely in a swelled state and not dissolved completely, and that copolymer A was not dissolved completely and in an ununiform state. The solvents were then removed in a rotary evaporator, and each of the resulting dried substances was placed between the receiver sheets made of polyethylene terephthalate, and compressed into a film of 0.3 mm thick (at 10 ton/ft$^2$ at 110° C. for 10 minutes). Each of the obtained films were designated as Comparative Examples 1-1 to 1-4.

Further, in Comparative Example 1-5, a film is prepared using only a 5 weight % SPU-1 solution in the same way as in Example 1-1.

In Comparative Example 1-6, 5 weight % SPU-1 solution and 5 weight % PC solution (Synthesis Example 1) were mixed in the ratio of 95:5 to prepare a homogeneous solution, and a film is prepared with this solution in the same way as in Example 1-1. The film thus obtained was subjected to the measurements to be described later.

Comparative Example 1-7

1 g of MPC, 0.5 g of polyvinyl alcohol (abbreviated as PVA hereinbelow) as a water-soluble polymer, and 0.05 g of N,N'-methylenebisacrylamide were dissolved in 8.5 ml of distilled water under agitation to prepare an aqueous solution. The aqueous solution thus obtained was subjected to filtration through a glass filter, deaerated under reduced pressure, and applied over the film prepared in Comparative Example 1-6 (the film of segmented polyurethane) to form a thin film. Subsequently, the thin film thus obtained was irradiated with the light from a 250 W high pressure mercury lamp for 3 hours for polymerization, thereby preparing a polyurethane film surface treated with MPC polymer disclosed in Japanese Laid-open Patent Application No. 59-43342. In other words, this film is a mixed polymer of MPC homopolymer free of hydrophobic monomer unit, and polyvinyl alcohol as a water-soluble polymer, coated on the segmented polyurethane. The film thus obtained was subjected to the measurements to be described later.

Comparative Example 1-8

A polymer film disclosed in Japanese Laid-open Patent Application No. 7-504459 was prepared, using PME (Synthesis Example 4) as copolymer A. That is, 1.1 g of PME (Synthesis Example 4) was mixed with 20 g of SPU-1, 40 g of ethyl acetate, and 40 g of propane-2-ol, and the turbidity of the resulting solution was measured by the method to be described later. Here, it was confirmed by visual observation that SPU-1 was slightly swelled and hardly dissolved. The solvents were then removed in a rotary evaporator, and the resulting dried substance was placed between the receiver sheets made of polyethylene terephthalate, and compressed into a film of 0.3 mm thick (at 10 ton/ft$^2$ at 100° C. for 10 minutes). The film thus obtained was subjected to the measurements to be described later.

Examples 2-1 to 2-3

In a solvent prepared by mixing dichloromethane and ethanol in the volume ratio of 7:3, SPU-1, SPU-2, PMC (Synthesis Example 3), PME (Synthesis Example 4), or PMU (Synthesis Example 7) was separately dissolved to prepare 5 weight % solutions. Then, SPU-1 solution and PMC solution, SPU-1 solution and PME solution, and SPU-2 solution and PMU solution were mixed respectively in the weight ratio of 95:5, and stirred for 30 minutes to prepare homogeneous solutions. Further, the homogeneous solutions were irradiated with ultrasonic wave using a probe type ultrasonic wave generator (trade name "Sonifier 250", manufactured by Branson, Danbury Conn., USA) at 20 KHz and the output of 200 W at scale 6 for 30 minutes. The turbidity of the resulting solutions was measured in the method to be described later.

Subsequently, 26.5 g of each solution was poured into a Teflon dish of the diameter of 75 mm, heated in a drier at 60° C. over night to remove the solvents, and further dried under reduced pressure to form polymer films. The compositions of the films are shown in Table 3 under Examples 2-1 to 2-3. The films were subjected to the measurements to be described later.

Comparative Examples 2-1 to 2-3

Films were prepared in the same way as in Examples 2-1 to 2-3 except that the solvent was changed to dichloromethane, and the resulting films were subjected to the same measurements. The compositions are shown in Table 3.

Example 3

The mixed homogeneous solution prepared in Example 2-2 was applied over the film prepared in Comparative Example 1-5 (the segmented polyurethane film) to form a thin film. The resulting thin film was heated in a drier at 60° C. over night to remove the solvent, and further dried under reduced pressure, thereby preparing a polyurethane film surface treated with a MPC-containing polymer composition. The resulting film was subjected to the measurements to be described later.

The procedure of the measurements carried out for Examples and Comparative Examples are described below.

[Measurement of Turbidity]

The turbidity of the solution was determined using a calorimeter ND-1001DP manufactured by NIPPON DENSHOKU KOGYO CO. LTD. by setting the state wherein the light is completely shielded as 100 whereas the state wherein only the solvent is charged in the cell as 0. The results are shown in Table 3.

From the results shown in Table 3, it is seen that the turbidity of the liquids prepared in Examples as starting materials was as low as 60% or lower, but the turbidity of the solutions wherein aggregates of the MPC polymer portions were recognized under the electron microscope was higher.

[Measurement of Glass-transition Temperature of Film]

Glass-transition temperature (Tg) of the films was determined by measurement using a differential scanning calorimetry (DSC). In particular, about 10 mg of the polymer film obtained was taken out, charged in an aluminum pan for DSC, sealed, and set in the prescribed position. Subsequently, the polymer film was first cooled down to −100° C. in liquid nitrogen, and then heated up to 300° C. at the programming rate of 10° C. per minute to measure the change in quantity of heat for determining the glass-transition temperature (Tg). The results are shown in Table 3.

From the results in Table 3, the lower glass-transition temperature due to the soft segment and the higher glass-transition temperature due to the hard segment were confirmed for the film made solely of SPU-1 in Comparative Example 1-5, indicating that phase separation occurred in the film. Further, the glass-transition temperatures due to the soft and hard segments of the polymer films prepared in Examples generally correspond to those of the film made solely of SPU-1. Accordingly, it is recognized that the phase separation characteristic of SPU-1 was maintained even after the polymer blending, and thus it is confirmed that the superior dynamic properties due to SPU-1 were also maintained. On the other hand, when PC, which does not contain the MPC unit, is used as copolymer A (Comparative Example 1-6), no definite glass-transition temperature was recognized. Accordingly, it is assumed that the two polymers are mutually dissolved, so that the superior dynamic properties due to SPU-1 cannot be exhibited.

[Observation of Polymer Film Surface under Electron Microscope]

It was confirmed under a scanning electron microscope (SEM, JSM-5400, JEOL, Tokyo) whether the phase separation is recognized between the phase of the hydrophobic polymer B and the domains of the copolymer A of several hundred micrometers or smaller in size distributed uniformly in the phase of the hydrophobic polymer B. First, the film was exposed to osmium tetroxide at the room temperature for 180 minutes to dye the MPC polymer portions, and subjected to sputtering with carbon (15–20 nm). Then the size of the domains of the dyed portions was observed under the electron microscope. The size of the domains is shown in Table 3.

In the film solely made of SPU-1 in Comparative Example 1-5, the domains of the dyed MPC polymer portions were not recognized, whereas in Examples, the domains of the MPC copolymer portions were recognized as white spots. It was confirmed that the size of the domains was within the range of about 1 to 50 $\mu$m, and that the phase-separated domains were distributed uniformly. It was further understood that the size of the domain was made still smaller by ultrasonic wave treatment (Examples 2-1 to 2-3). In Comparative Examples 1-1 to 1-4 or Comparative Examples 2-1 to 2-3, the liquid component in the starting material may not have been dissolved uniformly, and thus the MPC polymer portions were presented as aggregates. Accordingly, the phase separation in the order of several hundred micrometers or smaller could not have been achieved. In Comparative Example 1-6, the two polymers mixed may have been mutually dissolved completely, and thus no domain was observed. In Comparative Example 1-7, it was confirmed by the glass-transition temperature that the structure of hydrophobic polymer B was maintained in the film, but since the polymer mixture applied over the film dissolved mutually, the domains of the MPC copolymer portions were not observed.

TABLE 3

| Examples & Comparative Examples | Co-polymer A | Hydrophobic Polymer B | Content of Co-polymer A (wt %) | Turbidity of Solution (%) | Tg Lower (° C.) | Tg Higher (° C.) | Size of Domains (μm) |
|---|---|---|---|---|---|---|---|
| Ex. 1-1 | PMC | SPU-1 | 5 | 17.5 | −32 | 133 | 2-10 |
| Ex. 1-2 | PMC | SPU-1 | 10 | 38.4 | −30 | 134 | 1-15 |
| Ex. 1-3 | PME | SPU-1 | 5 | 18.0 | −31 | 134 | 2-10 |
| Ex. 1-4 | PME | SPU-1 | 10 | 39.6 | −29 | 134 | 1-10 |
| Ex. 1-5 | PMESi | SPU-1 | 5 | 19.3 | −32 | 133 | 2-15 |
| Ex. 1-6 | PMESi | SPU-1 | 10 | 42.1 | −30 | 135 | 2-20 |
| Ex. 1-7 | PMD | SPU-1 | 5 | 20.2 | −31 | 134 | 5-45 |
| Ex. 1-8 | PMU | SPU-2 | 5 | 19.6 | — | — | 3-18 |
| Ex. 1-9 | PMU | SPU-2 | 10 | 45.8 | — | — | 5-20 |
| Comp. Ex. 1-1 | PMC | SPU-1 | 5 | 64.4 | −31 | 133 | aggregate |
| Comp. Ex. 1-2 | PME | SPU-1 | 5 | 66.9 | −32 | 135 | aggregate |
| Comp. Ex. 1-3 | PMESi | SPU-1 | 5 | 79.8 | −31 | 132 | aggregate |
| Comp. Ex. 1-4 | PMD | SPU-1 | 5 | 82.4 | −31 | 133 | aggregate |
| Comp. Ex. 1-5 | none | SPU-1 | 0 | 3.6 | −30 | 133 | none |
| Comp. Ex. 1-6 | PC | SPU-1 | 5 | 3.5 | non-detectable | | none |
| Comp. Ex. 1-7 | MPC-PVA | SPU-1 | — | — | −30 | 133 | none |
| Comp. Ex. 1-8 | PME | SPU-1 | 5 | non-detectable | −30 | 134 | aggregate |
| Ex. 2-1 | PMC | SPU-1 | 5 | 17.2 | −31 | 134 | about 0.5 |
| Ex. 2-2 | PME | SPU-1 | 5 | 15.7 | −29 | 133 | about 0.5 |
| Ex. 2-3 | PMU | SPU-2 | 5 | 17.8 | — | — | about 0.5 |
| Comp. Ex. 2-1 | PMC | SPU-1 | 5 | 63.5 | −30 | 132 | aggregate |
| Comp. Ex. 2-2 | PME | SPU-1 | 5 | 64.3 | −31 | 133 | aggregate |
| Comp. Ex. 2-3 | PMU | SPU-2 | 5 | 66.7 | — | — | aggregate |
| Ex. 3 | PME | SPU-1 | 5 | — | −30 | 133 | about 1.0 |

[Analysis of Polymer Film Surface by XPS Analysis]

The surface analysis was conducted by XPS (X-ray photoelectron spectroscopy). P/C value (the value obtained by dividing the atomic weight of phosphorus on the surface of the sample by the sum of the atomic weight of phosphorus and carbon) was calculated from the peak areas obtained by the P 2p spectrum and the C 1s spectrum to confirm the density of the distribution of each MPC copolymer. In order to obtain information of the sample in the direction of depth, the electron take-off angle was set at 30 degree and 90 degree. The results are shown in Table 4.

By comparing the P/C values in Table 4, it was confirmed that phosphorus atoms in the phosphorylcholine group in MPC copolymer were present near the film surface and deep inside from the film surface when SPU-1 was mixed with PMC (Examples 1-1 and 1-2) or PME (Examples 1-3 and 1-4). Further, in the polymer film using PMC, the P/C value at the shallow location (30 degrees) was larger than that at the deep location (90 degrees), indicating that the phosphorylcholine group portions of the polymer film were distributed densely at the surface. On the other hand, in the polymer film using PME, the P/C values at 90 and 30 degrees do not differ widely from each other, indicating that the phosphorylcholine group portions were not remarkably distributed at the surface. It was understood that films of various surface properties may be designed by selecting the combination of the monomer having the side chain represented by the formula (1) and the hydrophobic monomer.

[Elusion of MPC copolymer from Polymer Film]

A polymer film of 0.3 mm thick was prepared, and a circular sample having the diameter of 1.5 cm was punched out of the film. The sample was soaked in 10 ml of distilled water and left stand still. At the third and the tenth day after the commencement of the soaking, 50 μl of the distilled water in which the film had been soaked was taken out, and the concentration of phosphorus was determined quantitatively in accordance with the composition determining method applied for MPC copolymer. Further, from the concentration of phosphorus, elusion ratio of MPC copolymer per unit volume of the film (mg/cm$^3$) was determined. The results are shown in Table 4.

From the results in Table 4, the elusion of MPC copolymer was hardly recognized from the polymer films of Examples after 10 days of soaking in water, and was only 8 wt % or lower. On the contrary, the elusion of MPC polymer was remarkable from the polymer films of Comparative Examples, in particular the elusion from the film prepared with the mixture containing the water-soluble polymer in Comparative Example 1-7 was considerable. Accordingly, it was revealed that the films of Examples have excellent properties in safety and durability.

TABLE 4

| Examples & Comparative Examples | Emission Angle of Photoelectron (degree) | P/C Value (Atomic ratio) | Elusion Test After 3 days | Elusion Test After 10 days |
|---|---|---|---|---|
| Example 1-1 | 30 | 3.09 | 0 | 0.7 |
|  | 90 | 1.85 |  |  |
| Example 1-2 | 30 | — | 0 | 2.2 |
|  | 90 | 3.25 |  |  |
| Example 1-3 | 30 | 2.60 | 0 | 2.3 |
|  | 90 | 2.77 |  |  |
| Example 1-4 | 30 | — | 5.1 | 7.7 |
|  | 90 | 1.84 |  |  |
| Example 1-5 | 30 | 2.70 | 0 |  |
| Example 1-6 | 30 | 2.75 | 0 | 0.2 |
| Example 1-7 | 30 | 2.88 | 4.8 | 7.9 |
| Example 1-8 | 30 | 2.75 | 0 | 1.4 |
| Example 1-9 | 30 | 2.77 | 0 | 1.7 |
| Comp. Ex. 1-1 | 30 | not uniform | 9.5 | 11.2 |
| Comp. Ex. 1-2 | 30 | not uniform | 8.9 | 10.5 |
| Comp. Ex. 1-3 | 30 | not uniform | 8.5 | 8.9 |
| Comp. Ex. 1-4 | 30 | not uniform | 13.5 | 15.7 |
| Comp. Ex. 1-5 | 30 | 0 | — | — |
|  | 90 | 0 |  |  |
| Comp. Ex. 1-6 | 30 | 0 | — | — |
| Comp. Ex. 1-7 | 30 | 0.22 | 21.5 | 23.0 |
| Comp. Ex. 1-8 | 30 | not uniform | 12.4 | 14.5 |
| Example 2-1 | 30 | 2.74 | 0 | 0.4 |
| Example 2-2 | 30 | 2.67 | 0 | 0.8 |
| Example 2-3 | 30 | 2.70 | 0 | 0.5 |
| Comp. Ex. 2-1 | 30 | not uniform | 8.3 | 8.4 |
| Comp. Ex. 2-2 | 30 | not uniform | 8.5 | 8.7 |
| Comp. Ex. 2-3 | 30 | not uniform | 8.2 | 8.4 |
| Example 3 | 30 | 2.57 | 4.3 | 7.5 |

[Dynamic Properties of Film]

Figure 1:
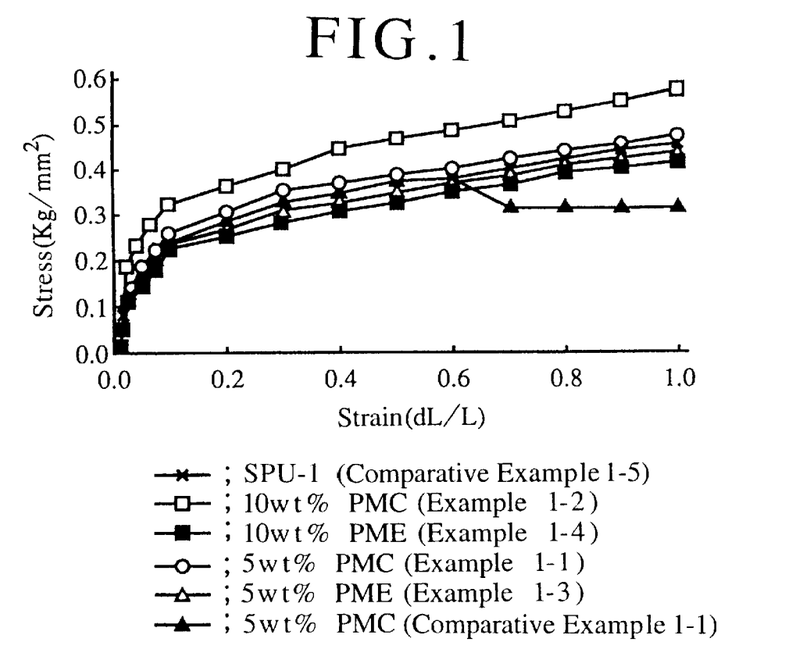
FIG. 1 is a graph showing stress-strain curves of uniform films of the high molecular compositions or a film made solely of SPU-1 or ununiform films measured in Examples and Comparative Examples.
Figure 2:
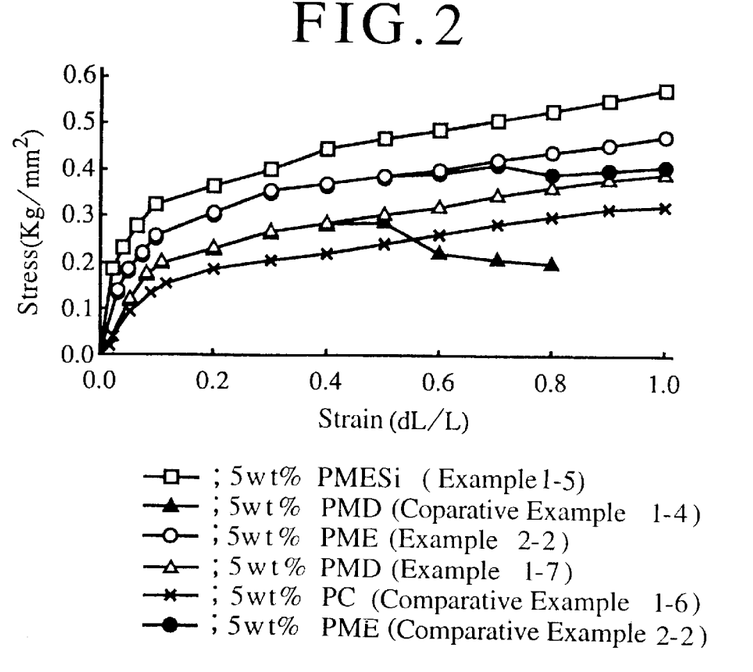
FIG. 2 is a graph showing stress-strain curves of uniform films of the high molecular compositions or ununiform films measured in Examples and Comparative Examples.

Polymer films of 5 mm wide, 10 mm long, and about 0.3 mm thick were subjected to tensile test at the tensile speed of 2 mm/min. One sample film was subjected to three times of measurements to calculate the average value, and a stress-strain curve was obtained. The results are shown in FIGS. 1 and 2. The stress-strain curves of the film solely made of SPU-1 in Comparative Example 1-5 and the ununiform films wherein MPC copolymer portions were aggregated were also obtained in the same way. The results are also shown in FIGS. 1 and 2. Further, the films solely made of the polymer in Synthesis Examples 1 and 2 were also subjected to the same test, but the films were too soft to complete the measurement. Therefore, it was confirmed that the dynamic strength of the films was absolutely insufficient.

From the stress-strain curves in FIG. 1, it was confirmed that the polymer films prepared by homogeneously dissolving MPC copolymer in SPU-1 and removing the solvent to cause phase separation with the domains being in size of several hundred micrometers or smaller (Examples 1-1 to 1-4) exhibit the same as or even better dynamic properties than those of the film solely made of SPU-1 (Comparative Example 1-5). Further, from the stress-strain curves in FIG. 2, it was confirmed that the film prepared with a monomer having a silyl group as a cross-linking component (Example 1-5) and the film subjected to the treatment with ultrasonic wave (Example 2-2) exhibit superior dynamic properties, whereas the film prepared with normal alkyl methacrylate, which has poor compatibility with SPU-1, as the hydrophobic monomer (Example 1-7) exhibited rather inferior dynamic properties. It was further confirmed that the ununiform films of Comparative Examples 1-4 and 2-2 wherein the MPC-containing portions were aggregated were prone to break and brittle. It was further confirmed that the film prepared from SPU-1 and PC wherein no phase separation was observed (Comparative Example 1-6) exhibited depression in stress, and good stress-strain curve cannot be obtained.

[Measurement of Adsorption of Plasma Protein By Polymer Film]

A Polymer film punched out in the form of a circle having the diameter of 1.5 cm was soaked in 10 ml of a phosphate buffer over night. The polymer film was then soaked in 20 ml of a phosphate buffer (prepared by dissolving 24.0 g of NaCl, 0.6 g of KCl, 8.7 g of $Na_2HPO_4.12H_2O$, and 0.6 g of $KH_2PO_4$ in 3 liter of distilled water) of albumin, γ-globulin, or fibrinogen having the same concentration as the human plasma protein concentration (albumin: 4.5 g/dl, γ-globulin: 1.6 g/dl, fibrinogen: 0.3 g/dl) or having one tenth the concentration as the human plasma protein concentration, and left stand still for 30 minutes. Subsequently, the polymer film was moved up and down ten times in 10 ml of the phosphate buffer for rinsing, and the residual solution on the polymer film was absorbed off with a filter paper. Next, the polymer film was soaked in 5 ml of a 1 weight % aqueous solution of sodium dodecyl sulfate to remove the adsorbed protein. The quantity of the removed protein was measured using a commercially available protein assay kit to determine the adsorbed amount per unit area. Incidentally, the measurement was conducted twice to calculate the average. In addition, the films in Examples, the film solely made of SPU-1 (Comparative Example 1-5), the film made of SPU-1 and PC (Comparative Example 1-6), and the coating film of MPC-PVA on the SPU-1 film (Comparative Example 1-7) were subjected to the same measurement. The results are shown in Table 5.

By comparing the polymer films of Examples and the film solely made of SPU-1 (Comparative Example 1-5) in Table 5, it is understood that the films of Examples absorbed less fibrinogen, which promotes adsorption of cells in blood such as thrombocytes, and has better properties in preventing absorption of biomaterials. It was also confirmed that the treatment with ultrasonic wave is also effective in suppressing the adsorption of protein.

[Evaluation of Biocompatibility of Polymer Film]

In this test, the following evaluations were made with regard to one of the most representative biocompatibility, namely, blood compatibility.

A polymer film punched off in the form of a circle having the diameter of 1.5 cm was soaked in a phosphate buffer over night. The phosphate buffer was removed immediately before the test, and 0.7 ml of previously prepared whole blood of rabbit or plate rich plasma of rabbit (PRP: prepared by mixing 9 ml of rabbit blood with 1 ml of a 3.8 weight % aqueous solution of sodium citrate, and centrifuged at 750 rpm for 15 minutes) was added and left stand still. The whole blood was contacted for 60 and 120 minutes, and PRP was contacted for 60 minutes with the polymer film. Subsequently, the whole blood or PRP of rabbit was removed, and the sample was rinsed three times with the phosphate buffer. Then, 1.0 ml of a 2.5 volume % glutaraldehyde solution was added to the sample, and left stand still for 2 hours to fix the hemocytes. After removing glutaraldehyde, the sample was rinsed three times with distilled water, and soaked in liquid nitrogen for freeze drying. Subsequently, gold was sputtered over the sample to observe the surface under a scanning electron microscope. The results are shown in Table 5. Further, the same measurement was carried out for each Example, the film solely made of SPU-1 (Comparative Example 1-5), the film made of the mixture of SPU-1 and PC (Comparative Example 1-6), and the coating film of MPC-PVA over the SPU-1 film (Comparative Example 1-7). The results are also shown in Table 5.

From Table 5, it was revealed that the polymer films of Examples exhibited suppressed adhesion of blood cells thereto compared to Comparative Examples, and thus were highly compatible to blood and useful as a medical material.

(1)

wherein $R^1$, $R^2$ and $R^3$ are the same or different groups and stand for a hydrogen atom or an alkyl group having 1 to 4 carbon atoms, and a hydrophobic monomer selected from the group consisting of a (meth)acrylate of an alkyl alcohol having 5 to 15 carbon atoms, an alicyclic alkyl (meth)acrylate, an alkyl (meth)acrylate having a urethane bond,

TABLE 5

| Examples & Comparative | Absorption of Plasma Protein ($\mu$g/cm$^2$) | | | | | | Blood Compatibility | | |
|---|---|---|---|---|---|---|---|---|---|
| | Concentration of Human Plasma Protein | | | Concentration of Human Plasma Protein (1/10) | | | Blood 60 | Blood 120 | PRP 60 |
| Examples | Albumin | γ-globulin | Fibrinogen | Albumin | γ-globulin | Fibrinogen | min. | min. | min. |
| Ex. 1-1 | 4.27 ± 1.43 | 3.64 ± 1.19 | 1.57 ± 0.63 | 1.57 ± 0.36 | 1.17 ± 0.10 | 1.03 ± 0.43 | − | − | − |
| Ex. 1-2 | 3.53 ± 1.50 | 4.57 ± 1.71 | 1.41 ± 0.38 | 1.23 ± 0.07 | 1.86 ± 0.16 | 0.71 ± 0.13 | − | − | − |
| Ex. 1-3 | 3.53 ± 1.50 | 4.57 ± 1.71 | 1.41 ± 0.38 | 1.23 ± 0.07 | 0.86 ± 0.16 | 0.71 ± 0.13 | − | − | − |
| Ex. 1-4 | 4.36 ± 0.24 | 4.86 ± 1.64 | 1.57 ± 0.38 | 1.40 ± 0.13 | 1.29 ± 0.23 | 0.43 ± 0.59 | − | − | − |
| Ex. 1-5 | 3.50 ± 1.52 | 4.45 ± 1.64 | 1.52 ± 0.41 | 1.33 ± 0.08 | 0.82 ± 0.21 | 0.73 ± 0.22 | − | − | − |
| Ex. 1-6 | 4.30 ± 0.22 | 4.34 ± 1.55 | 1.45 ± 0.27 | 1.37 ± 0.22 | 1.32 ± 0.19 | 0.44 ± 0.45 | − | − | − |
| Ex. 1-7 | 4.52 ± 1.32 | 3.30 ± 0.35 | 1.68 ± 0.45 | 1.67 ± 0.53 | 1.45 ± 0.19 | 0.95 ± 0.05 | − | − | − |
| Ex. 1-8 | 3.53 ± 1.35 | 4.17 ± 1.15 | 1.92 ± 0.55 | 1.39 ± 0.26 | 1.02 ± 0.22 | 0.95 ± 0.21 | − | − | − |
| Ex. 1-9 | 3.43 ± 1.85 | 4.11 ± 1.15 | 1.30 ± 0.35 | 1.31 ± 0.09 | 1.02 ± 0.22 | 0.92 ± 0.21 | − | − | − |
| Comp. Ex. 1-1 | 4.57 ± 1.44 | 3.65 ± 1.24 | 1.87 ± 0.53 | 1.67 ± 0.46 | 1.32 ± 0.11 | 1.11 ± 0.33 | ++ | ++ | +++ |
| Comp. Ex. 1-2 | 3.72 ± 1.10 | 4.45 ± 1.25 | 2.05 ± 0.43 | 1.53 ± 0.17 | 1.16 ± 0.23 | 0.99 ± 0.23 | ++ | ++ | +++ |
| Comp. Ex. 1-3 | 3.68 ± 1.52 | 4.49 ± 1.62 | 2.12 ± 0.31 | 1.53 ± 0.18 | 0.99 ± 0.22 | 1.11 ± 0.23 | ++ | ++ | +++ |
| Comp. Ex. 1-4 | 4.72 ± 1.52 | 3.33 ± 0.32 | 2.08 ± 0.55 | 1.88 ± 0.63 | 1.48 ± 0.18 | 1.02 ± 0.08 | ++ | ++ | +++ |
| Comp. Ex. 1-5 | 4.71 ± 1.71 | 3.14 ± 0.45 | 2.29 ± 0.70 | 1.71 ± 0.43 | 1.50 ± 0.16 | 1.00 ± 0.16 | ++ | ++ | +++ |
| Comp. Ex. 1-6 | 5.33 ± 1.82 | 4.82 ± 0.55 | 3.58 ± 0.99 | 2.43 ± 0.55 | 2.23 ± 0.18 | 1.72 ± 0.20 | +++ | +++ | +++ |
| Comp. Ex. 1-7 | 5.29 ± 1.66 | 4.99 ± 0.43 | 3.60 ± 1.11 | 2.33 ± 0.39 | 2.31 ± 0.20 | 1.65 ± 0.15 | +++ | +++ | +++ |
| Comp. Ex. 1-8 | 4.64 ± 1.88 | 3.13 ± 0.52 | 2.11 ± 0.72 | 1.89 ± 0.64 | 1.51 ± 0.19 | 1.05 ± 0.11 | +++ | +++ | +++ |
| Ex. 2-1 | 4.01 ± 1.24 | 3.52 ± 1.20 | 1.42 ± 0.54 | 1.47 ± 0.35 | 1.08 ± 0.12 | 0.75 ± 0.35 | − | − | − |
| Ex. 2-2 | 3.35 ± 1.46 | 4.46 ± 1.55 | 1.37 ± 0.35 | 1.19 ± 0.10 | 0.77 ± 0.09 | 0.78 ± 0.12 | − | − | − |
| Ex. 2-3 | 3.33 ± 1.25 | 4.10 ± 1.25 | 1.32 ± 0.25 | 1.33 ± 0.16 | 0.98 ± 0.21 | 0.88 ± 0.11 | − | − | − |
| Comp. Ex. 2-1 | 4.50 ± 1.22 | 3.60 ± 1.14 | 1.57 ± 0.55 | 1.65 ± 0.36 | 1.12 ± 0.23 | 1.09 ± 0.32 | ++ | ++ | +++ |
| Comp. Ex. 2-2 | 3.52 ± 0.52 | 4.55 ± 0.75 | 2.00 ± 0.61 | 1.45 ± 0.27 | 1.09 ± 0.33 | 0.95 ± 0.43 | ++ | ++ | +++ |
| Comp. Ex. 2-3 | 3.60 ± 1.12 | 4.33 ± 1.02 | 2.02 ± 0.35 | 1.46 ± 0.28 | 1.06 ± 0.26 | 1.01 ± 0.33 | ++ | ++ | +++ |
| Ex. 3 | 4.55 ± 1.49 | 4.51 ± 1.82 | 2.52 ± 0.36 | 1.50 ± 0.11 | 1.30 ± 0.21 | 0.95 ± 0.15 | − | − | − |

In Table 5:
−: Little adhesion of blood cells containing thrombocyte
++: Some adhesion of blood cells containing thrombocyte
+++: Lots of adhesion of thrombocyte

What is claimed is:

1. A high molecular material characterized in that said material is a mixed material produced by solidification of a liquid high molecular composition comprising: a copolymer A produced by copolymerization of a monomer composition containing a (meth)acrylate of a alkyl alcohol having 1 to 4 carbon atoms having a side chain represented by the formula (1) and mixtures thereof: a hydrophobic polymer B containing a segmented polyurethane; and a mixed solvent consisting of a halogenated hydrocarbon solvent and a lower alcohol solvent; said liquid high molecular composition having turbidity of 60% or less, wherein the structure of said mixed material shows phase separation in which domains of several hundred micrometers or less in size consisting of the copolymer A are uniformly distributed in a phase consisting of said hydrophobic polymer B.

2. The high molecular material as claimed in claim 1 wherein said segmented polyurethane comprises a segmented polyurethane selected from the group consisting of a segmented polyurethane obtained by polyaddition of dicyclohexylmethane diisocyanate and polyether diol, a segmented polyurethane obtained by polyaddition of diphenylmethane diisocyanate and polyether diol, and mixtures thereof.

3. The high molecular material as claimed in any of claim 1 wherein content of said copolymer A is 1 to 30 wt % of the total amount of said copolymer A and said hydrophobic polymer B.

4. A liquid high molecular composition for producing a mixed high molecular material produced by solidification of a liquid high molecular composition containing: a copolymer A produced by copolymerization of a monomer composition containing a (meth)acrylate of an alkyl alcohol having 1 to 4 carbon atoms having a side chain represented by the formula (1)

(1)

wherein $R^1$, $R^2$ and $R^3$ are the same or different groups and stand for a hydrogen atom or an alkyl group having 1 to 4 carbon atoms, and a hydrophobic monomer selected from the group consisting of a (meth)acrylate of an alkyl alcohol having 5 to 15 carbon atoms, an alicyclic alkyl (meth)acrylate, an alkyl (meth)acrylate having an urethane bond, and mixtures thereof; a hydrophobic polymer B containing a segmented polyurethane selected from the group consisting of a segmented polyurethane obtained by polyaddition of dicyclohexylmethane diisocyanate and polyether diol, a segmented polyurethane obtained by polyaddition of diphenylmethane diisocyanate and polyether diol, and mixtures thereof; and a mixed solvent consisting of a halogenated hydrocarbon solvent and a lower alcohol solvent, said liquid high molecular composition having a turbidity of 60% or less, wherein the structure of said mixed material shows phase separation in which domains of several hundred micrometers or less in size consisting of the copolymer A are uniformly distributed in a phase consisting of said hydrophobic polymer B, said liquid high molecular composition comprising said copolymer A, said drophobic polymer B and said mixed solvent, and having turbidity of 60% or less.

5. A medical material wherein said material contains a mixed material produced by solidification of a liquid high molecular composition comprising: a copolymer A produced by copolymerization of a monomer composition containing a (meth)acrylate of an alkyl alcohol having 1 to 4 carbon atoms having a side chain represented by the formula (1)

(1)

wherein $R^1$, $R^2$ and $R^3$ are the same or different groups and stand for a hydrogen atom or an alkyl group having 1 to 4 carbon atoms, and a hydrophobic monomer selected from the group consisting of a (meth)acrylate of a branched alkyl alcohol having 5 to 15 carbon atoms, an alicyclic alkyl (meth)acrylate, an alkyl (meth)acrylate having an urethane bond and mixtures thereof; a hydrophobic polymer B containing a segmented polyurethane selected from the group consisting of a segmented polyurethane obtained by polyaddition of dicyclohexylmethane diisocyanate and polyether diol, a segmented polyurethane obtained by polyaddition of diphenylmethane diisocyanate and polyether diol, and mixtures thereof; and a mixed solvent consisting of a halogenated hydrocarbon solvent and a lower alcohol solvent; said liquid high molecular composition having turbidity of 60% or less, wherein the structure of said mixed material shows phase separation in which domains of several hundred micrometers or less in size consisting of said copolymer A are uniformly distributed in a phase consisting of said hydrophobic polymer B.

6. A method for producing a liquid high molecular composition containing: a copolymer A produced by copolymerization of a monomer composition containing a (meth)acrylate of an alkyl alcohol having 1 to 4 carbon atoms having a side chain represented by the formula (1)

(1)

wherein $R^1$, $R^2$ and $R^3$ are the same or different groups and stand for a hydrogen atom or an alkyl group having 1 to 4 carbon atoms, comprising irradiating a solution comprising:

a. a copolymer A produced by copolymerization of a monomer composition containing a (meth)acrylate of an alkyl alcohol having 1 to 4 carbon atoms having a side chain represented by the formula (1) and a hydrophobic monomer selected from the group consisting of a (meth)acrylate of an alkyl alcohol having 5 to 1 5 carbon atoms, an alicyclic alkyl (meth)acrylate, an alkyl (meth)acrylate having an urethane bond, and mixtures thereof;

b. a hydrophobic polymer B containing a segmented polyurethane; and C. a mixed solvent consisting of the halogenated hydrocarbon solvent and a lower alcohol solvent, with an ultrasonic wave to adjust the turbidity of the solution to 60% or less.

* * * * *

UNITED STATES PATENT AND TRADEMARK OFFICE
CERTIFICATE OF CORRECTION

PATENT NO. : 5,977,257
DATED : November 2, 1999
INVENTOR(S) : Kazunori Waki; Kazuo Matsuyama; Nobuo Nakabayashi; Kazuhiko Ishihara It is certified that error appears in the above-identified patent and that said Letters Patent is hereby corrected as shown below:

Column 23,
Line 65, please change "a alkyl" to -- an alkyl --.

Column 25,
Line 7, please delete "any of".
Line 48, please change "drophobic" to -- hydrophobic --.

Column 26,
Line 51, please change "; and c. a mixed" to --; and c. a mixed --.

Signed and Sealed this

Sixteenth Day of October, 2001

Attest:

NICHOLAS P. GODICI
Attesting Officer    Acting Director of the United States Patent and Trademark Office